United States Patent [19]

Kiel et al.

[11] Patent Number: 4,940,819
[45] Date of Patent: Jul. 10, 1990

[54] PROCESS FOR THE HYDROGENATION OF α,β-UNSATURATED KETONES

[75] Inventors: Wolfgang Kiel, Odenthal; Heinz Ziemann, Leichlingen, both of Fed. Rep. of Germany

[73] Assignee: Bayer Aktiengesellschaft, Leverkusen, Fed. Rep. of Germany

[21] Appl. No.: 375,763

[22] Filed: Jul. 5, 1989

[30] Foreign Application Priority Data

Jul. 20, 1988 [DE] Fed. Rep. of Germany ....... 3824625

[51] Int. Cl.$^5$ .............................................. C07C 45/62
[52] U.S. Cl. ..................................... 568/318; 568/350; 568/396
[58] Field of Search ............... 568/316, 318, 348, 350, 568/394, 396

[56] References Cited

U.S. PATENT DOCUMENTS

| | | | |
|---|---|---|---|
| 2,674,634 | 4/1954 | Greensfelder et al. | 568/396 |
| 3,366,646 | 1/1968 | Dewhirst | 568/396 |
| 3,574,764 | 4/1971 | Gregory et al. | 568/396 |
| 3,929,891 | 12/1975 | Habig et al. | 564/417 |
| 4,020,108 | 4/1977 | Ehmann | 568/396 |
| 4,041,083 | 8/1977 | Gradeff et al. | 568/350 |
| 4,260,829 | 4/1981 | Horner et al. | 568/396 |

FOREIGN PATENT DOCUMENTS

| | | | |
|---|---|---|---|
| 2150220 | 4/1973 | Fed. Rep. of Germany | 564/417 |
| 2549900 | 5/1977 | Fed. Rep. of Germany | 564/447 |
| 2362133 | 3/1978 | France | 568/396 |

*Primary Examiner*—James H. Reamer
*Attorney, Agent, or Firm*—Sprung Horn Kramer & Woods

[57] ABSTRACT

The catalytic hydrogenation of α,β-unsaturated ketones of the formula $$R^1—CH=CH—CO—R^2,$$

in which $R^1$ and $R^2$ independently of one another represent straight-chain or branched alkyl, hydroxy-alkyl, alkenyl, cycloalkyl, cycloalkenyl, aralkyl or aryl, where at least one of the radicals $R^1$ and $R^2$ is monosubstituted to trisubstituted by halogen, can be carried out on a Ni-containing catalyst and in the presence of an organic sulphur compound of the formula $$R^3—S(=O)_n—R^4$$

in which $R^3$ and $R^4$ independently of one another denote straight-chain or branched alkyl, hydroxy-alkyl, carboxyalkyl or phenyl, and furthermore $R^3$ and $R^4$ may together represent —CH=CH—CH=CH—, —(CH$_2$)$_4$—, —(CH$_2$)$_5$—, —(CH$_2$)$_2$—S—(CH$_2$)$_2$— or —(CH$_2$)$_2$—O—(CH$_2$)$_2$—, $R^4$ may additionally denote hydrogen or CO—C$_1$–C$_{12}$-alkyl and n assumes the value 0 or 1.

17 Claims, No Drawings

PROCESS FOR THE HYDROGENATION OF α,β-UNSATURATED KETONES

BACKGROUND OF THE INVENTION

1. Field of the Invention

The invention relates to a process for the catalytic hydrogenation of the C=C double bond of α,β-unsaturated ketones, which have at least one substituent containing bonded halogen, to give the corresponding saturated ketones. This hydrogenation is carried out on Ni-containing catalysts and in the presence of an organic sulphur compound.

2. Description of the related Art

In the selective hydrogenation of C=C bonds in the presence of other functional groups, the lability of halogen substituents, for example, in particular in basic medium, has to be taken into account; even fluorine is cleavable in the presence of nickel (Houben-Weyl, *Methoden* [Methods], 4th edition, vol. 4/1c (1980), 155). Even with the simultaneous presence of carbonyl groups, in this case particularly with α,β-unsaturated ketones, undesired hydrogenation of the oxo group has to be taken into account (Houben-Weyl, loc. cit., p. 162); this undesired reaction is observed more strongly with Ni catalysts than with Pd catalysts (P. Rylander, Catalytic Hydrogenation in Organic Synthesis 1979, p. 51).

Even in the catalytic hydrogenation of aromatic nitro compounds to give the respective arylamines, cleavage of simultaneously present, aromatically bonded halogen is observed. In order to suppress such a cleavage of halogen, the noble metal catalysts employed for such hydrogenations were modified. To this end, a procedure can be used in which a separately prepared modified catalyst is employed or in which a modifying agent is added to the reaction mixture as such. Thus, sulphides of the noble metals were employed in GB No. 1,064,959; DE-OS (German Published Specification) No. (2,105,780 describes a Pt/C contact with $Na_2SO_3$ doping; DE-OS (German Published Specification) No. 2,150,220 describes noble metal/activated carbon/sulphoxide catalysts. DE-AS (German Published Specification) No. 2,549,900 describes the hydrogenation of chloro-nitro aromatic compounds using noble metal catalysts and with the addition of thioethers as modifying agents.

The use of modifying agents such as those described is always combined with a decrease in the catalyst activity which frequently leads to relatively long hydrogenation times or requires the use of more severe reaction conditions. For the unproblematic hydrogenation of nitro compounds, the reduced catalyst activity is in fact always completely sufficient, which was not to be expected for the hydrogenation of C=C double bonds.

With complicated hydrogenation problems, such as, for example, the hydrogenation of a C=C double bond with the retention of an oxo group and the avoidance of hydrogenolytic cleavage of halogen, as in the present case, a non-uniform course of the hydrogenation thus had to be taken into account, in particular since with α,β-unsaturated ketones, frequently either an undesired hydrogenation of the carbonyl group is observed or in order to avoid this undesired reaction incomplete hydrogenation of the double bond has to be taken into account.

SUMMARY OF THE INVENTION

A process for the catalytic hydrogenation of α,β-unsaturated ketones of the formula $$R^1-CH=CH-CO-R^2 \qquad (I).$$

in which $R^1$ and $R^2$ independently of one another represent straight-chain or branched $C_1-C_{12}$-alkyl or $C_2-C_{12}$-hydroxyalkyl, straight-chain or branched $C_2-C_{12}$-alkenyl, $C_3-C_8$-cycloalkyl, $C_3-C_8$-cycloalkenyl, $C_7-C_{14}$-aralkyl or $C_6-C_{12}$-aryl, where at least one of the radicals $R^1$ and $R^2$ is monosubstituted to trisubstituted by halogen, to give the respective saturated ketones of the formula $$R^{11}-CH_2-CH_2-CO-R^{12} \qquad (II).$$

in which $R^{11}$ and $R^{12}$ assume the meaning of $R^1$ and $R^2$ with the exception that alkenyl and cycloalkenyl are hydrogenated to the respective alkyl or cycloalkyl, has now been found, which is characterized in that a Ni-containing catalyst is employed and that the reaction is carried out in the presence of an organic sulphur compound of the formula $$R^3-S(=O)_n-R^4 \qquad (III)$$

in which $R^3$ and $R^4$ independently of one another denote straight-chain or branched $C_1-C_{12}$-alkyl, hydroxy-$C_2-C_{12}$-alkyl, carboxy-$C_1-C_{12}$-alkyl or phenyl, and furthermore $R^3$ and $R^4$ together may represent —CH=CH—CH=CH—, —$(CH_2)_4$—, —$(CH_2)_5$—, —$(CH_2)_2$—S—$(CH_2)_2$— or —$(CH_2)_2$—O—$(CH_2)_2$—, $R^4$ may additionally denote hydrogen or CO—$C_1-C_{12}$-alkyl and n assumes the value 0 or 1.

DETAILED DESCRIPTION OF THE INVENTION

Straight-chain or branched $C_1-C_{12}$-alkyl is, for example, methyl, ethyl, propyl, isopropyl, butyl, isobutyl, tert.-butyl, amyl, hexyl, octyl, decyl or dodecyl; $C_1-C_6$-alkyl is preferred, $C_1-C_4$-alkyl particularly preferred. Hydroxyalkyl carries a hydroxyl group in any position, preferably in the ω-position, and may furthermore be interrupted in the carbon chain by ether oxygen. Carboxy-alkyl carries a carboxyl group in any position, preferably in the α- or ω-position. The same preferred ranges apply as for alkyl.

Straight-chain or branched $C_2-C_{12}$-alkenyl is, for example, vinyl, propenyl, butenyl, isobutenyl, pentenyl, hexenyl, octenyl, decenyl or dodecenyl; $C_2-C_6$-alkenyl is preferred. $C_2-C_4$-alkenyl particularly preferred.

$C_3-C_8$-cycloalkyl is, for example, cyclopropyl, cyclobutyl, cyclopentyl, cyclohexyl, cycloheptyl or cyclooctyl which can be substituted by one or two methyl or ethyl groups; substituted or unsubstituted cyclopropyl, cyclopentyl or cyclohexyl are preferred.

$C_3-C_8$-cycloalkenyl is, for example, cyclopropenyl, cyclobutenyl, cyclopentenyl, cyclohexenyl, cycloheptenyl or cyclooctenyl.

$C_7$-$C_{14}$-aralkyl is, for example, benzyl, phenylethyl, naphthylmethyl, naphthylethyl, biphenyl-methyl or biphenyl-ethyl, preferably benzyl or phenylethyl.

$C_6$-$C_{12}$-aryl is, for example, phenyl, naphthyl or biphenyl, preferably phenyl.

At least one of the radicals in the $\alpha,\beta$-unsaturated ketone is monosubstituted to trisubstituted by halogen, such as fluorine, chlorine or bromine, preferably fluorine or chlorine, particularly preferably chlorine. In the case of multiple substitution, this may be substitution by different halogen atoms.

All aromatic radicals mentioned may furthermore carry one or two methyl or ethyl groups, or methoxy or ethoxy groups, and also the hydroxyl group.

In a preferred manner, $\alpha,\beta$-unsaturated ketones of the formula $$R^5-CH=CH-CO-R^6 \quad (IV)$$

are employed in which
$R^5$ and $R^6$ independently of one another denote straight-chain or branched $C_1$-$C_6$-alkyl, $C_2$-$C_6$-alkenyl, cyclopropyl, cyclopentyl, cyclohexyl, benzyl, phenylethyl or phenyl, where at least one of the radicals $R^5$ and $R^6$ represents phenyl and where furthermore at least one of the radicals $R^5$ and $R^6$ is monosubstituted to trisubstituted by halogen.

Further preferred ketones are those of the formula $$R^7-CH=CH-CO-R^8 \quad (IV).$$

in which
$R^7$ denotes phenyl and
$R^8$ denotes straight-chain or branched $C_1$-$C_6$-alkyl, $C_2$-$C_6$-alkenyl, cyclopropyl, benzyl or phenyl,
where at least one of the radicals $R^7$ and $R^8$ is monosubstituted to trisubstituted by halogen.

Further preferred ketones are 5-halophenyl-2,2-dimethylpent-4-en-3-ones, particularly 5-(4-chlorophenyl)-2,2-dimethyl-pent-4-en-3-one, and 6-halophenyl-3,3-dimethylhex-5-en-4-ones.

All $\alpha,\beta$-unsaturated ketones are in each case distinguished by at least one substituent which is substituted by halogen.

The $\alpha,\beta$-unsaturated ketones to be employed can be prepared via the known aldol condensation. They have 3 functional groups available: C=C double bond, carbonyl group and (at least one) halogen. The preparation, the desired hydrogenation and the undesired side reaction may be represented by the example of 5-(4-chlorophenyl)-2,2-dimethyl-pent-4-en-3-one; in the case of an alcoholic hydrogenation medium, alcohol addition to the double bond must furthermore be suspected:

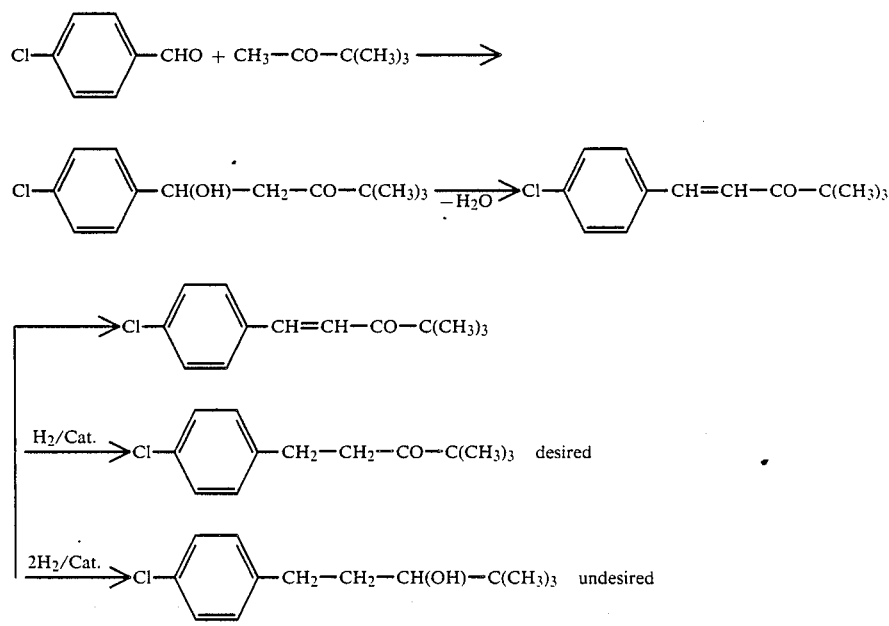

-continued

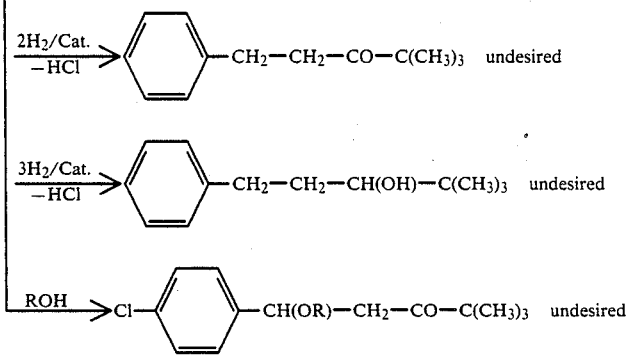

In this case, it is insignificant whether the undesired substances are formed directly from the α,β-unsaturated ketone or by simultaneous additional reaction of the desired saturated ketone.

The process according to the invention is carried out in the presence of one or more organic sulphur compounds of the formula (III). Examples of such compounds are bis-(2hydroxyethyl) sulphide, bis-(2-hydroxypropyl) sulphide, thiodiacetic acid and its alkali metal salts, thioanisole, thiodipropionic acid, its salts and its dimethyl ester, diphenyl sulphide, dithiane, thioxane, thiophene, benzothiazole, dimethyl sulphoxide, methyl ethyl sulphoxide and diethyl sulphoxide. The organic sulphur compound is employed in an amount from 0.002–0.1 parts by weight, preferably 0.01–0.075 parts by weight, per part by weight of catalyst.

In a preferred manner, an organic sulphur compound of the formula $$R^{13}-S(=O)_n-R^{14}$$

is employed in which
R$^{13}$ and R$^{14}$ independently of one another denote alkyl, hydroxy-C$_2$-C$_{12}$-alkyl or carboxy-C$_1$-C$_{12}$-alkyl, and where
R$^{14}$ additionally may denote CO—C$_1$-C$_6$-alkyl and n assumes the value 0 or 1.

In a particularly preferred manner, bis-(2-hydroxyethyl) sulphide is employed.

The addition of the organic sulphur compound is carried out together with the catalyst, before the addition or after the addition of the catalyst. If the catalyst is reused repeatedly, the organic sulphur compound in general only needs to be added to the catalyst or to the reaction mixture on the first use. The catalyst then retains its high specific activity together with a constant high yield even after repeated use many times or in a continuous procedure. A subsequent addition of the organic sulphur compound is possible, but generally only necessary, if fresh catalyst is added in place of some-what consumed or exhausted catalyst.

Hydrogenation catalysts employed according to the invention are Ni-containing, such as Ni on supports, Ni in the form of elemental nickel sponge, Ni oxide, Raney nickel and others. Supports are, for example, SiO$_2$, Al$_2$O$_3$, pumice, carbon and other supports known to those skilled in the art. However, in a preferred manner, Raney catalysts, such as Raney nickel, Raney nickel-iron, Raney nickel-cobalt or Raney nickel-iron-cobalt in anhydrous or even water-moist or solvent-moist form are employed.

The reaction medium employed may be alcohols, such as methanol, ethanol, isopropanol, butanol, aliphatic or aromatic hydrocarbons, such as toluene, xylene, cyclohexane, isooctane and the like, ethers, such as tetrahydrofuran, dioxane or methyl tert.-butyl ether, esters, such as ethyl acetate and lastly the reaction product itself if it is liquid at the reaction temperature. A proportion of water (for example up to 20% by weight of the total reaction medium) does not interfere, particularly if the reaction medium is water-soluble.

The hydrogenation is carried out at 30°–250° C., preferably at 50°–140° C., and an H$_2$ pressure of 3–200 bar, preferably 10–150 bar. In a preferred variant, the process according to the invention is carried out by the addition of a basic substance at a pH of 8–14. Basic substances in this connection are, for example, sodium hydroxide, potassium hydroxide, calcium hydroxide (for example in the form of slaked lime), calcium oxide, potassium carbonate, sodium carbonate, sodium acetate, or aliphatic or heterocyclic amines. The basic substances may, if they are water-soluble, be employed as aqueous solution or as solid. In a preferred manner, aqueous sodium hydroxide solution is employed.

In a surprising manner, such an addition of basic substances in no way promotes halogen cleavage. In addition, the side reaction of alcohol addition to the C=C double bond, observed when alcoholic reaction media are used, is suppressed.

The basic substance is added in an amount from 0.001–0.025 parts by weight, preferably 0.002–0.01 parts by weight, per part by weight of the α,β-unsaturated ketone.

In general, the process is carried out in such a way that the starting material, the reaction medium, the catalyst, the organic sulphur compound and, if desired, the base are initially introduced into a hydrogenation autoclave and after sealing the reactor the air is displaced with nitrogen and then the nitrogen with hydrogen. After completion of the reaction, the reaction vessel is first depressurized and emptied; the catalyst is filtered off and may be reused without a new addition of organic sulphur compound.

The process can be carried out both batchwise and continuously.

The process may furthermore be applied both to the pure, unsaturated α,β-unsaturated ketones and to a crude reaction mixture, for example from the aldol condensation, in which such α,β-unsaturated ketones can be obtained from an aldehyde and a methyl ketone.

It is surprising that through the use of the organic sulphur compound as a modifying agent, for which a deactivation is normally observed, the described hydrogenation takes place more selectively, more reproducibly and, in particular, more completely than without this addition; in particular it is surprising that the hydrogenation also takes place more rapidly than without addition, i.e. the hydrogenation activity is increased, whereas usually deactivation takes place by sulphur compounds. The catalysts have a high stability.

EXAMPLES

General procedure

The chlorinated α,β-unsaturated keto compound, the solvent, the catalyst and the organic sulphur compound (with the exception of the comparison examples) and, if desired, a base were initially introduced into an autoclave.

The autoclave was first flushed with nitrogen and then with hydrogen.

The mixture was then heated to the temperature indicated and hydrogenated at the hydrogen pressure indicated, until absorption of hydrogen no longer took place.

After completion of the reaction, the catalyst was filtered off: it could then be directly prepared for further hydrogenations. The chlorinated saturated ketones were isolated from the filtrate by customary methods (for example by distillation).

EXAMPLES 1 to 9 (EXAMPLES 1, 4, 6 and 8 for comparison)

Hydrogenation of 139 g of 5-(4-chlorophenyl)-2,2-dimethylpent-4-en-3-one in 245 g of methanol or toluene at 100° C. on 5.6 g of Raney nickel with and without addition of bis-(2-hydroxyethyl) sulphide to give 5-(4-chlorophenyl)- 2,2-dimethylpentan-3-one (final product).

The catalyst contained either about 50% of water or 50% of toluene.

TABLE 1

| Example No. | Solvent | Addition | $H_2$ (bar) | Reaction time | Dechlorinated compound | Starting compound | Final product |
|---|---|---|---|---|---|---|---|
| 1 | Methanol | — | 150 | 10 Min. | 1.8% | <0.1% | 97.3% |
| 2 | Methanol | 0.2 g | 150 | 3 Min. | 0.4% | 0.15 | 99.3% |
| 3 | Methanol | 0.7 g | 150 | 3 Min. | 0.1% | <0.1% | 99.1% |
| 4 | Toluene | — | 150 | 20 Min. | 1.1% | 6.0% | 89.3% |
| 5 | Toluene | 0.7 g | 150 | 3 Min. | 0.1% | 0.1% | 98.4% |
| 6 | Methanol | — | 10 | 55 Min. | 1.6% | 36.8% | 60.7% |
| 7 | Methanol | 0.7 g | 10 | 159 Min. | 0.3% | 0.1% | 99.0% |
| 8 | Toluene | — | 10 | 15 Min. | 1.2% | 73.5% | 24.6% |
| 9 | Toluene | 0.7 g | 10 | 41 Min. | 0.2% | 0.1% | 97.7% |

EXAMPLES 10 and 11

Hydrogenation of 139 g of 5-(4-chlorophenyl)-2,2-dimethylpent-4-en-3-one in 245 g of methanol at 100° C. and 150 bar of $H_2$ on 5.6 g of Raney nickel (water-moist) with the addition of 0.7 g of bis-(2-hydroxyethyl) sulphide with the addition of 45% strength aqueous sodium hydroxide solution. Before filling the autoclave, this batch was stirred at 80° C. for 30 min. in a mashing vessel.

TABLE 2

| Example No. | NaOH (45% strength) | Dechlor. compound | Methoxy adduct to the C—C double bond | Starting compound | Final comp. |
|---|---|---|---|---|---|
| 10 | — | 0.7% | 6.0% | 0.9% | 92.0% |
| 11 | 1.23 g | 0.4% | — | 0.05% | 99.0% |

EXAMPLES 12 to 19

Repeated hydrogenation of 139 g of 5-(4-chlorophenyl)-2,2-dimethyl-pent-4-en-3-one several times in 245 g of methanol at 100° C. and 150 bar of $H_2$ on in each case recovered Raney nickel with a single addition of 0.7 g of bis-(2-hydroxyethyl) sulphide to the 1st batch. 1.23 g of 45% strength NaOH solution were added to each batch.

TABLE 3

| Example | Catalyst recovered | Reaction time | Dechlorinated compound | Methoxy compound | Starting compound | Final product |
|---|---|---|---|---|---|---|
| 12 | from Ex. 11 | 0.1 h | 0.3% | — | <0.1% | 99.3% |
| 13 | from Ex. 12 | 0.1 h | 0.1% | — | <0.1% | 99.5% |
| 14 | from Ex. 13 | 0.1 h | 0.1% | — | <0.1% | 99.5% |
| 15 | from Ex. 14 | 0.1 h | 0.1% | — | <0.1% | 99.2% |
| 16 | from Ex. 15 | 0.15 h | 0.2% | — | <0.1% | 99.1% |
| 17 | from Ex. 16 | 0.18 h | 0.1% | — | <0.1% | 99.2% |
| 18 | from Ex. 17 | 0.18 h | 0.1% | — | <0.1% | 98.6% |
| 19 | from Ex. 18 | 0.18 h | 0.1% | — | 0.4% | 98.9% |

EXAMPLES 20-26

Following the procedure of Example 1, 120 g of 5-(4-chlorophenyl)-2,2-dimethylpent-4-en-3-one were hydrogenated in 180 g of methanol at 110° C. and 150 bar $H_2$ pressure in the presence of the additives indicated. The hydrogenation time was uniformly fixed at 6 min. The hydrogenations, recognizable from the consumption of $H_2$ in general began at room temperature, in Example 26 the hydrogenation began at 80° C., in Example 29 at 55° C. The results are assembled in the table below. The composition of the reaction products was determined by gas chromatography.

C. and 80 bar hydrogen pressure in the course of 25 minutes in 2000 g of methanol.

TABLE 4

| | | | Examples 20 to 26 | | | |
|---|---|---|---|---|---|---|
| Example | Addition amount (g)/type | Final product (%) | Starting compound (%) | Dechlorinated compound (%) | Methoxy compound (%) | Further by-products (%) |
| 20 | 0.2 CH$_3$—CO—SH | 98.9 | 0.1 | 0.6 | 0.3 | 0.1 |
| 21 | 0.2 HO—C$_2$H$_4$—SH | 99.3 | 0.1 | 0.4 | <0.1 | <0.1 |
| 22 | 0.2 HO—C$_2$H$_4$—S—C$_2$H$_5$ | 99.3 | 0.1 | 0.5 | 0.1 | — |
| 23 | 0.2 Thiophene | 98.9 | 0.1 | 0.6 | 0.3 | <0.1 |
| 24 | 0.2 S(CH$_2$—COOH)$_2$ | 99.3 | 0.1 | 0.4 | 0.2 | — |
| 25 | 0.2 OS(CH)$_3$)$_2$ | 99.7 | <0.1 | 0.2 | <0.1 | <0.1 |
| 26 | 0.2 CH$_3$COSC$_6$H$_5$ | 99.8 | <0.1 | 0.1 | <0.1 | <0.1 |

EXAMPLE 27

In accordance with the procedure described in Example 1, 63 g of the α,β-unsaturated ketone of the formula

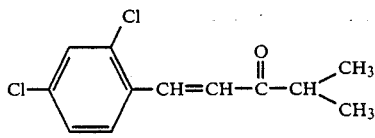

were hydrogenated on 10 g of Raney nickel-iron with the addition of 0.45 g of bis-(2-hydroxyethyl) sulphide at 50° C. and 80 bar hydrogen pressure in the course of 15 minutes in 300 g of tetrahydrofuran.

The reaction product contained, according to gas chromatographic analysis, 97% of the saturated ketone of the formula

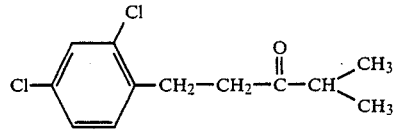

and only 0.4% of dechlorinated compounds.

EXAMPLE 28

In accordance with the procedure described in Example 1, 500 g of the α,β-unsaturated ketone of the formula

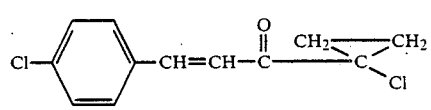

were hydrogenated on 25 g of Raney nickel with the addition of 1.25 g of bis-(2-hydroxyethyl)sulphide at 70°

The reaction product contained, according to gas chromatographic analysis, 98.5% of the saturated ketone of the formula

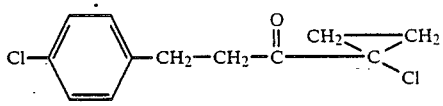

and only 0.5% of dechlorinated compounds.

COMPARISON EXAMPLES 29–32

In accordance with the procedure described in Example 1, in each case 120 g of 5-(4-chlorophenyl)-2,2-dimethyl-pent-4-en-3-one were hydrogenated on 3 g of 5% strength palladium-charcoal in the presence of the amounts of bis-(2-hydroxyethyl) sulphide indicated in the table at 50° C. and 100 bar H$_2$ pressure in 210 g of methanol. The composition of the reaction products determined by gas chromatography and the respective hydrogenation times are summarized in the table below.

The results of Examples 29–32 show that no selective hydrogenation of the C,C-double bond in the presence of halogen substituents and the ketone group which can be hydrogenated to the carbinol is possible using a palladium catalyst with addition of an organic sulphur compound. As is evident, it is possible to substantially suppress the dehalogenation using relatively high additions combined with a considerably increased hydrogenation time, but the hydrogenation of the carbonyl group could not be excluded.

TABLE 5

| | | Comparison examples 29–32 | | | |
|---|---|---|---|---|---|
| | | | Composition of the reaction product [%]* | | |
| Example | Thioether [g] | Reaction time [min] | Final product | Dechlorinated compounds | Carbinol from keto group |
| 29 | 0.015 | 10 | 38 | 19 | 40 |
| 30 | 0.03 | 15 | 49 | 8 | 41 |
| 31 | 0.15 | 80 | 43.5 | 4.5 | 50 |
| 32 | 0.30 | 105 | 74 | 0.7 | 24 |

*Starting compound was not found; the residue consists to 100% of non-identified by-products

What is claimed is:

1. A process for the catalytic hydrogenation of α,β-unsaturated ketones of the formula

R$^1$—CH=CH—CO—R$^2$, in which

R$^1$ and R$^2$ independently of one another represent straight-chain or branched C$_1$-C$_{12}$-alkyl or C$_2$-C$_{12}$-hydroxyalkyl, straight-chain or branched C$_2$-C$_{12}$-alkenyl, C$_3$-C$_8$-cycloalkyl, C$_3$-C$_8$- cycloalkenyl, $C_7$-$C_{14}$-aralkyl or $C_6$-$C_{12}$-aryl, where at least one of the radicals $R^1$ and $R^2$ is monosubstituted to trisubstituted by halogen,
to give the respective saturated ketones of the formula $$R^{11}-CH_2-CH_2-CO-R^{12},ps$$

in which
$R^{11}$ and $R^{12}$ assume the meaning of $R^1$ and $R^2$ with the exception that alkenyl and cycloalkenyl are hydrogenated to the respective alkyl or cycloalkyl,
wherein the hydrogenation is carried out in the presence of a Ni-containing catalyst and an organic sulphur compound of the formula $$CH_3-CO-SH$$

or of the formula $$R^3-S(=O)_n-R^4$$

in which
$R^3$ and $R^4$ independently of one another denote straight-chain or branched $C_1$-$C_{12}$-alkyl, hydroxy-$C_2$-$C_{12}$-alkyl, or carboxy-$C_1$-$C_{12}$-alkyl or phenyl, and furthermore
$R^3$ and $R^4$ together may represent $-CH=CH-CH=CH-$, $-(CH_2)_4-$, $-(CH_2)_5-$, $-(CH_2)_2-S-(CH_2)_2-$ or $-(CH_2)_2-O-(CH_2)_2-$,
$R^4$ may additionally denote hydrogen or $CO-C_1$-$C_{12}$-alkyl and
n assumes the value 0 or 1 and wherein the Ni-containing catalyst is Ni on supports, Ni in the form of elemental nickel sponge, Ni oxide or a Raney nickel.

2. The process according to claim 1, wherein the organic sulphur compound is of the formula $$R^{13}-S(=O)_n-R^{14}$$

in which
$R^{13}$ and $R^{14}$ independently of one another denote straight-chain or branched $C_1$-$C_{12}$-alkyl, hydroxy-$C_2$-$C_{12}$-alkyl or carboxy-$C_1$-$C_{12}$-alkyl, and where $R^{14}$ additionally may denote $CO$-$C_1$-$C_8$-alkyl and
n assumes the value 0 or 1.

3. The process according to claim 2, wherein the sulphur compound is bis-(2-hydroxyethyl) sulphide.

4. The process according to claim 1, wherein the catalyst is Raney nickel, Raney nickel-iron, Raney nickel-cobalt or Raney-nickel-iron-cobalt.

5. The process according to claim 1, wherein the reaction is carried out at a pH of 8-14.

6. The process according to claim 1, wherein the $\alpha,\beta$-unsaturated ketone is of the formula $$R^5-CH=CH-CO-R^6$$

in which
$R^5$ and $R^6$ independently of one another denote straight-chain or branched $C_1$-$C_6$-alkyl, $C_2$-$C_6$-alkenyl, cyclopropyl, cyclopentyl, cyclohexyl, benzyl, phenylethyl or phenyl, where at least one of the radicals $R^5$ and $R^6$ represents phenyl and where furthermore at least one of the radicals $R^5$ and $R^6$ is monosubstituted to trisubstituted by halogen.

7. The process according to claim 6, wherein the $\alpha,\beta$-unsaturated ketone is of the formula $$R^7-CH=CH-CO-R^8$$

in which
$R^7$ denotes phenyl and
$R^8$ denotes straight-chain or branched $C_1$-$C_6$-alkyl, $C_2$-$C_6$-alkenyl, cyclopropyl, benzyl or phenyl,
where at least one of the radicals $R^7$ and $R^8$ is monosubstituted to trisubstituted by halogen.

8. The process according to claim 6, wherein the ketone is a 5-halophenyl-2,2-dimethyl-pent-4-en-3-one or a 6-halophenyl 3,3-dimethyl-hex-5-en-4-one.

9. The process according to claim 1, wherein the reaction it is carried out at 30°-250° C.

10. The process according to claim 9, wherein the reaction it is carried out at 50°-140° C.

11. The process according to claim 1, wherein the reaction is carried out at an $H_2$ pressure of 3-200 bar.

12. The process according to claim 11, wherein the reaction it is carried out at an $H_2$ pressure of 10-150 bar.

13. The process according to claim 5, wherein the pH value is adjusted by the addition of from 0.001-0.025 parts by weight per part by weight of the $\alpha,\beta$-unsaturated ketone of a basic substance.

14. The process according to claim 13, wherein 0.002-0.01 parts by weight of the basic substance are added.

15. The process according to claim 13, wherein the basic substance is sodium hydroxide, calcium oxide, potassium carbonate, sodium carbonate, sodium acetate, or aliphatic or heterocyclic amines.

16. The process according to claim 13, wherein the basic substance is employed as aqueous solution or as solid.

17. The process according to claim 16, the basic substance is aqueous sodium hydroxide solution.

* * * * *

UNITED STATES PATENT AND TRADEMARK OFFICE
CERTIFICATE OF CORRECTION

PATENT NO. : 4,940,819

DATED : July 10, 1990

INVENTOR(S) : Kiel et al.

It is certified that error appears in the above-identified patent and that said Letters Patent is hereby corrected as shown below:

Title Page      FOREIGN PATENT DOCUMENTS: After " 2549900, 5/1977, Fed Rep. of Germany, 564/ " delete " 447 " and substitute -- 417 --

Col. 11, claim 1 line 6      After " $R^{12}$, " delete " ps "

Col. 11, claim 2 line 45      Delete " $C_8$ " and substitute -- $C_6$ --

Signed and Sealed this

Seventh Day of April, 1992

Attest:

HARRY F. MANBECK, JR.

*Attesting Officer*      *Commissioner of Patents and Trademarks*